United States Patent
Fernandez

(10) Patent No.: US 9,028,750 B2
(45) Date of Patent: May 12, 2015

(54) FUMIGATION SYSTEM AND PROCESS WITH TEMPERATURE CONTROL, FILTRATION, AND AIR-REINTRODUCTION

(71) Applicant: Manuel A. Fernandez, Miami, FL (US)

(72) Inventor: Manuel A. Fernandez, Miami, FL (US)

(73) Assignee: Florida East Coast Industries, Inc., Coral Gables, FL (US)

( * ) Notice: Subject to any disclaimer, the term of this patent is extended or adjusted under 35 U.S.C. 154(b) by 18 days.

(21) Appl. No.: 13/925,389

(22) Filed: Jun. 24, 2013

(65) Prior Publication Data

US 2014/0112827 A1 Apr. 24, 2014

Related U.S. Application Data

(60) Provisional application No. 61/716,462, filed on Oct. 19, 2012.

(51) Int. Cl.
*A61L 9/00* (2006.01)
*A61L 2/00* (2006.01)
*A01M 13/00* (2006.01)
*A01N 25/18* (2006.01)

(52) U.S. Cl.
CPC ............... *A01M 13/00* (2013.01); *A01N 25/18* (2013.01); *A01M 13/003* (2013.01)

(58) Field of Classification Search
CPC ............... A61L 2/00; A61L 2/22; A61L 9/03; A23L 3/00
USPC ............. 422/1, 28, 30, 32–33, 295, 298, 300, 422/305–307; 43/125, 129
See application file for complete search history.

(56) References Cited

U.S. PATENT DOCUMENTS 3,097,916 A 7/1963 Dawson
5,417,921 A 5/1995 Dove
(Continued)

FOREIGN PATENT DOCUMENTS

GB 2 323 785 10/1998
JP 10-156139 6/1998
JP 2007-504949 3/2007

OTHER PUBLICATIONS

USDA Treatment Manual, United States Department of Agriculture, dated May 2012.
(Continued)

*Primary Examiner* — Monzer R Chorbaji
(74) *Attorney, Agent, or Firm* — Mayback & Hoffman, P.A.; Gregory L. Mayback; Rebecca A. Tie

(57) ABSTRACT

Fumigation systems and processes that are especially applicable for the fumigation of perishable (or otherwise sensitive to temperature) agricultural products as the temperature conditions under which the product is being treated are closely controlled to advantageously prevent the product from being exposed to temperature drops and/or spikes during the fumigation cycle. In addition, the present invention incorporates an air filtration system as a part of the fumigation system to substantially remove the toxic fumigant residuals from the air before it is exhausted into the open atmosphere, which typically occurs at the completion of a fumigation cycle. As such, the harmful effect of the fumigant on the products and the surrounding environment and work areas is greatly minimized. In summary, the systems and processes of the present invention provide the ability to conduct fumigations in a well-controlled environment.

18 Claims, 8 Drawing Sheets

(56) References Cited

U.S. PATENT DOCUMENTS

| | | | |
|---|---|---|---|
| 5,565,178 A | 10/1996 | Dove | |
| 6,047,497 A | 4/2000 | Smithyman | |
| 6,513,282 B2 | 2/2003 | Schott | |
| 7,910,056 B2 | 3/2011 | Ivanine | |
| 2001/0029695 A1* | 10/2001 | Schott et al. | 43/129 |
| 2004/0107707 A1 | 6/2004 | Richardson | |
| 2007/0084105 A1 | 4/2007 | Lindsay | |

OTHER PUBLICATIONS

International Search Report and Written Opinion dated Feb. 21, 2014 of International App. No. PCT/US13/65171.

* cited by examiner

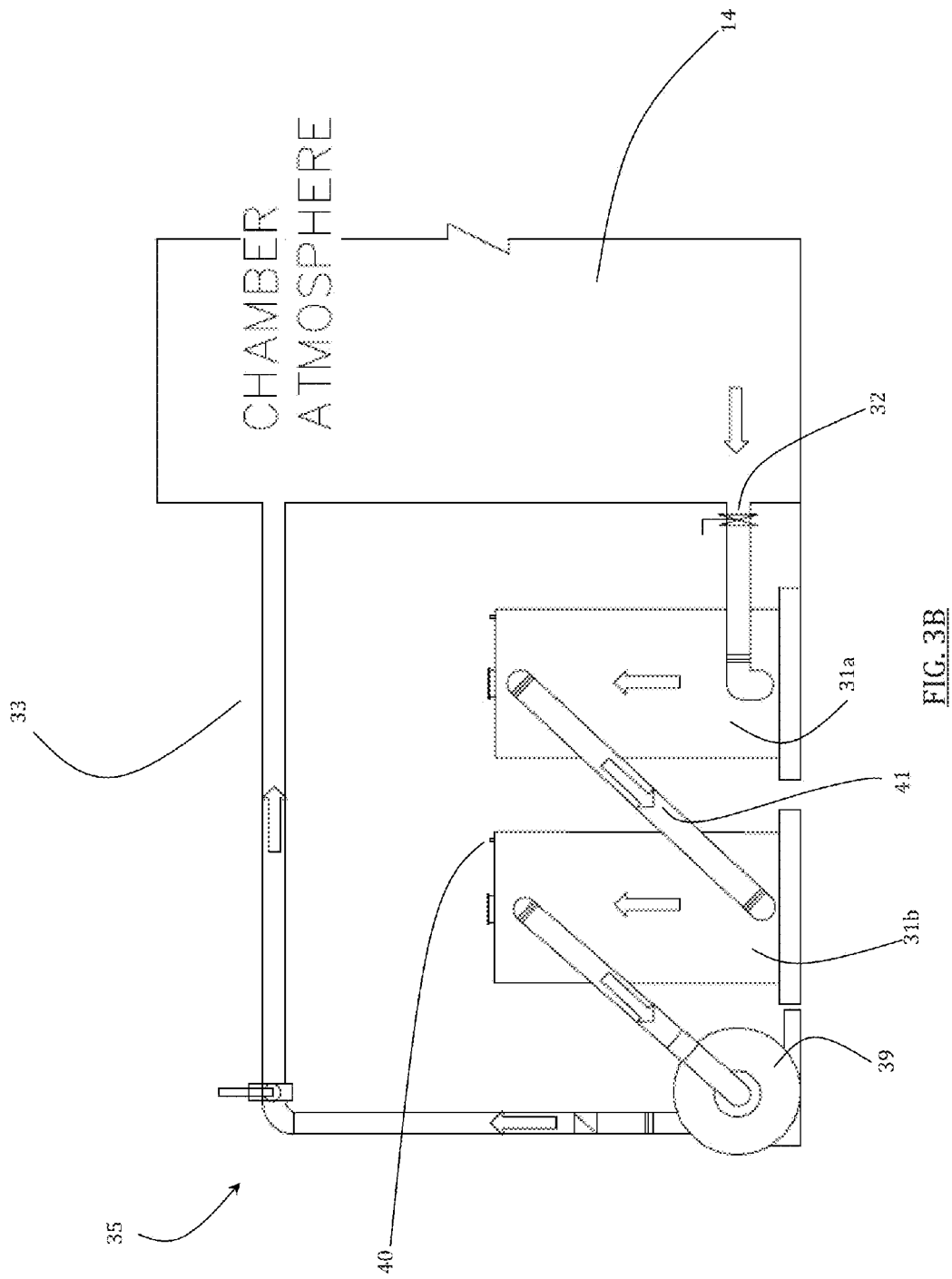

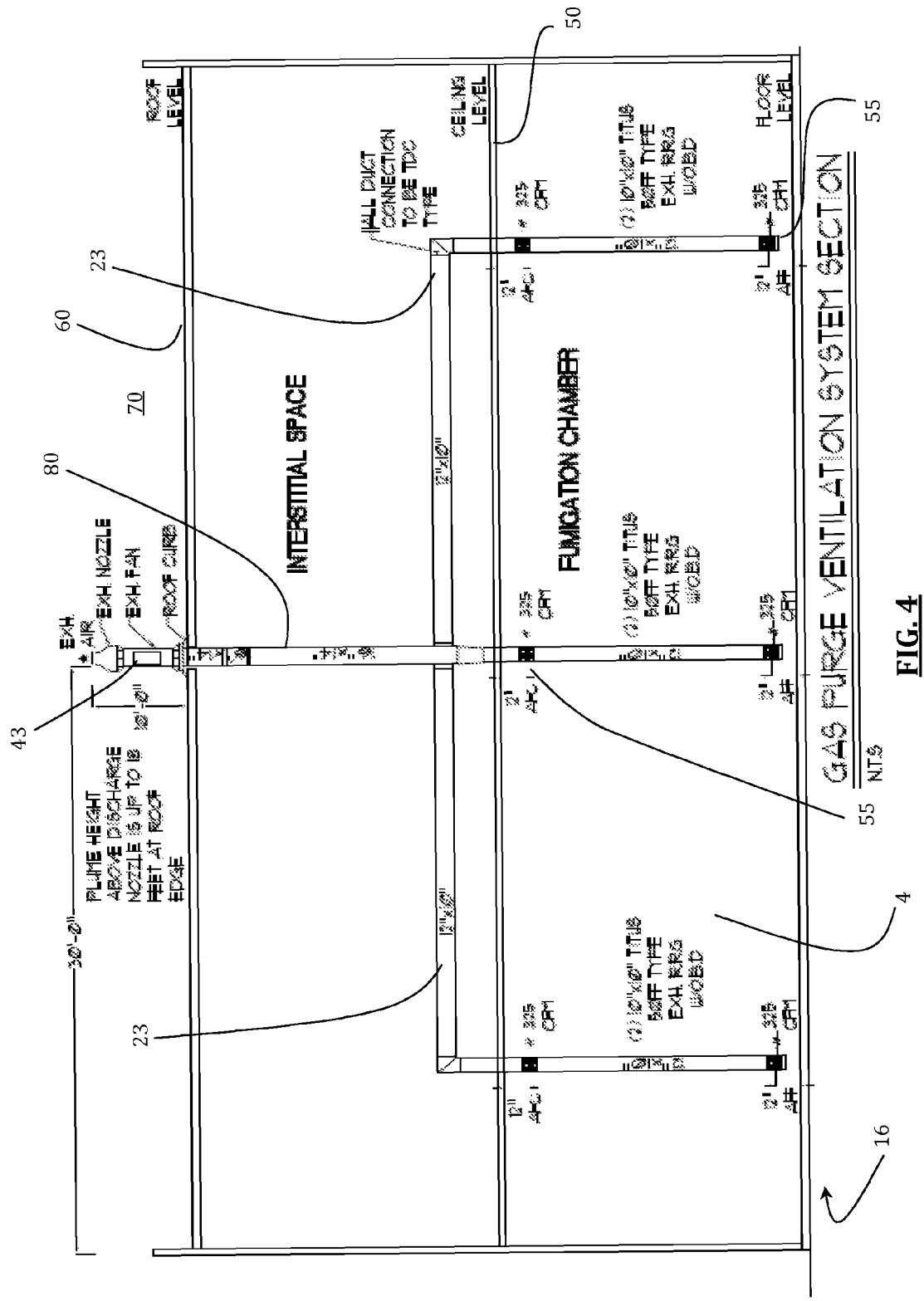

FUMIGATION SYSTEM AND PROCESS WITH TEMPERATURE CONTROL, FILTRATION, AND AIR-REINTRODUCTION

CROSS-REFERENCE TO RELATED APPLICATIONS

This application claims the priority, under 35 U.S.C. §119, of U.S. Provisional Patent Application Ser. No. 61/716,462, filed Oct. 19, 2012, the entire disclosure of which is hereby incorporated herein by reference in its entirety.

FIELD OF THE INVENTION

The present invention lies in the field of fumigation of imported and exported products at their points of entry and exit (or shipping and receiving). In particular, the present invention provides systems and processes that are especially applicable for the fumigation of perishable (or otherwise sensitive to temperature) agricultural products as the temperature conditions under which the product is being treated are closely controlled to advantageously prevent the product from being exposed to temperature drops and/or spikes during the fumigation cycle. In addition, the present invention incorporates an air filtration system as a part of the fumigation system to substantially remove the toxic fumigant residuals from the air before it is exhausted into the open atmosphere, which typically occurs at the completion of a fumigation cycle. As such, the harmful effect of the fumigant on the products and the surrounding environment and work areas is greatly minimized. In summary, the systems and processes of the present invention provide the ability to conduct fumigations in a well-controlled environment.

BACKGROUND OF THE INVENTION

As provided for by government regulatory agencies, such as the United States Department of Agriculture (USDA), lumber, logs, fruits, vegetables, and other perishable agricultural commodities or products that are imported into or exported out of the regulated territory are mandatorily quarantined and treated, at their point of entry or exit, according to specific protocols and treatment schedules set by the one or more regulatory agencies. This treatment occurs to prevent the introduction, movement and infestation of certain agricultural pests and other target organisms into or within the regulated territory. Such pests include insects, mites and ticks, nematodes, snails and slugs, fungi, and various other vermin. To comply with this regulatory requirement, there are a number of treatment processes that are currently known and used in the industry. One category of treatment processes is chemical treatments that include the use of fumigants and aerosols and/or micronized dusts. The term "fumigation," as defined in the USDA Treatment Manual, is the release and dispersion of a toxic chemical in such a way so as to reach the target organism in a gaseous state.

By way of example, in the United States, nearly every aspect, ranging from the equipment used to the various steps of the fumigation process itself, is carefully inspected and strictly dictated in USDA regulations and guidelines. The fumigation enclosure is inspected to ensure, for example, that it is well-ventilated and has specific aeration capabilities. Furthermore, due to the high toxicity of the fumigants, a fumigation enclosure must be sealed and airtight when in use and, therefore, it is meticulously tested for leaks in and around the enclosure and the operation equipment.

Further, with respect to the USDA, the fumigation process itself is also carefully monitored. For example, the USDA sets forth a specific dosage rate of the fumigant depending upon the temperature of the product and the type of product being treated. There are also certain restrictions on the amount of volume of a product that can be treated in a given fumigation enclosure. And, specific stages of the process (e.g., the period of time during which air circulation blowers or fans are to be turned off to allow the fumigant to effectively settle in order to take an accurate chemical concentration reading), are also set forth by the USDA. During the fumigation process itself, the fumigant concentration level in the air within the fumigation enclosure is monitored to ensure that effective levels of the fumigant are maintained during the appropriate stages of the process and, thereafter, to ensure that the concentration level has fallen to within safe acceptable limits during aeration of the fumigation enclosure at the completion of the process.

Furthermore, the USDA routinely inspects the product itself to ensure and certify its quality at various points in time before, during and after the fumigation process, according to specific regulations. For example, with respect to fruits and vegetables, the USDA will take a sample number of the product and measure the temperature of the samples to determine whether or not the product temperature is within an acceptable temperature range for that particular fruit or vegetable (e.g., approximately 40° F.) according to the individual USDA treatment schedule that is specific to that type of fruit or vegetable. Depending on the particular product, an elevated temperature may indicate that the product is now in a deteriorating condition.

Within the realm of quarantining and fumigating imported and exported commodities that include perishable agricultural products, there are several methods that are well-known to persons of skill in the art and, for example, are specifically defined and approved of by the USDA. These methods include: (1) tarpaulin fumigation, (2) sealed container or open container (with the addition of a tarpaulin) fumigation, and (3) chamber fumigation, using either a normal atmospheric pressure (NAP) chamber or a vacuum chamber. Depending upon the specific circumstances in each case, such as the nature and dimensions of the product, one fumigation method may be more suitable than another. Below is a brief summary, in simple general terms, of each of these three methods. As described in detail below, in each instance, agency regulations typically require that a restrictive perimeter be maintained around the fumigation site for specific periods of time during the fumigation process and that a specific period of time must be allowed for aerating the fumigation enclosure into the open atmosphere before the product may be released at the completion of the fumigation process.

In tarpaulin fumigation, which is a relatively primitive process, a flexible tarp is secured and sealed over and around cargo that has typically been arranged in a square or rectangular shaped stack. To permit air movement along the floor and between the various cargo, the cargo is arranged on pallets or in open containers before being surrounded by the tarp. To seal the tarp around the cargo in order to prevent the fumigant gas from leaking out from under the tarp, sand snakes are oftentimes used to weight down the fringe of the tarp to the floor. The fumigant gas is then administered under the tarp using gas introduction lines and is distributed amongst the cargo using circulation fans having the capacity to move a certain volume (in cubic feet per minute) until a prescribed amount of gas has been administered and distributed inside the tarp. Once the fumigant has taken its full effect, fans are used to aerate the air from beneath the tarp and up into the open atmosphere until a prescribed amount of time has passed and the gas concentration readings indicate that the fumigant concentration level has fallen below a certain regulatory threshold level. Following this active aeration process, the cargo is "passively" aerated by simply removing the tarp and allowing the cargo to air out before it is finally released. Ordinarily, this kind of fumigation process is conducted at ambient temperatures, which can be detrimental to the perishables being treated depending on the climate conditions of the geographical location.

Container fumigation is conducted similarly to tarpaulin fumigation, but instead is conducted inside a container that is typically comprised of an ocean container or a domestic trailer containing palletized cargo. The container is placed in a well-ventilated area and is effectively sealed with either its doors closed, or, the container is left open and is sealed under a tarp. All of the vents of the container are sealed. Thereafter, the fumigant gas is introduced into the container using a gas line that is attached to a rear gasket of the container. The gas is then circulated inside the container using axial-type blade fans that have been installed inside the container. At the completion of the process, the container doors are opened and the circulation fans are turned on to expel the toxic air up into the open atmosphere until a prescribed amount of time has passed and gas concentration readings indicate that the fumigant concentration level has fallen below a certain regulatory threshold level.

In chamber fumigation, the fumigation enclosure is comprised of a specially designed and constructed normal atmospheric pressure (NAP) chamber or a vacuum chamber. Inside the chamber are circulation fans and an exhaust system. Prior to operation, the integrity of the chamber is tested by pressurizing the chamber and, thereafter, the chamber is inspected for any resultant pressure leaks. The chamber pressure is then relieved. Once the chamber is approved for use, cargo is loaded into the chamber. Depending on the type of product and the way in which it was packaged during shipping, pallets are either loaded directly into the chamber or, alternatively, the pallets are left inside their shipping container and the entire shipping container itself is loaded into the chamber such that the pallets and the container are fumigated simultaneously. Once the chamber is sealed, the fumigant is inducted into the chamber. The fumigant gas is circulated inside the chamber for a certain period of time. Using the exhaust system, the chamber is then aerated up into the open atmosphere until gas concentration readings indicate that the fumigant concentration level has fallen below a certain regulatory threshold level. In the case of a vacuum chamber, the vacuum remaining at the end of the fumigation is brought to zero by temporarily opening an air intake valve. The valve is then closed in order to draw a vacuum, and then the vacuum is released again. This process is repeated for as many times as necessary to adequately aerate the chamber.

Irrespective of the particular process that is used, fumigation remains to be a highly effective method for eliminating pests and other undesirable organisms from agricultural products. However, due to the characteristics of the fumigants themselves and the need for a fumigation enclosure, importers, exporters and the agricultural commodity industry at large face a particularly difficult challenge in preserving the fragile nature of perishable goods and handling the toxicity inherently present throughout the fumigation process.

For example, because fumigation requires a sealed enclosure in order to contain the fumigant so that it can reach and maintain an effective concentration that is, unfortunately, extremely toxic and most certainly fatal, the agricultural product must be loaded and unloaded into the sealed enclosure as described above. Also, because the fumigant is a gas, it must be evenly distributed and well-dispersed amongst the units of the agricultural product to be effective. Yet, in some cases, depending on the type of agricultural product, the products are transported and kept in certain packaging to protect them from being physically damaged (e.g. squeezed or crushed), or to limit their exposure to light and heat that may induce premature spoiling of the product. However, if the packaging is not readily permeable by the fumigant, as is the case with certain plastic wrappings that include cellophane, films, shrink wrap, and waxed, laminated, or waterproofed papers, the packaging must be perforated, removed, or opened before fumigation. Therefore, to ensure the maximum effectiveness of the fumigation, products are often unduly handled and/or exposed, which may harm the quality and appearance of the product.

In another example, the USDA has indicated that less fumigant is required when fumigating at higher temperatures thereby suggesting that fumigants are most effective when used at certain temperatures. Therefore, in treatment schedules, for example, that are specific to each type of agricultural product, the USDA prescribes a lowermost temperature point or range for the product temperature while inside the fumigation enclosure. For example, with respect to certain grape varieties, the individual USDA treatment schedule for that product provides that its product temperature cannot fall below 40° F. This lowermost temperature point of 40° F. is common to a relative majority of agricultural products. Thus, in logical terms, with the exception of cold climate areas during their cool season(s), most, if not all existing fumigation processes are conducted at ambient temperatures. However, many perishable agricultural products are intentionally stored, shipped, and/or transported in refrigeration, which is generally below 40° F., to extend their shelf life by either preserving the product at its peak ripeness or by delaying or stunting its ripening stage. The advent of refrigeration revolutionized the agricultural commodity industry by making it possible to have a perishable product that is not locally grown (or produced), nonetheless, reach an end consumer in its best condition, which is essential to the success of any product. Yet, in order to be fumigated in temperatures at or above, for example, 40° F., as is dictated by, for example, USDA treatment schedules, these products must be brought out of refrigeration and, as a result, are exposed to variable temperature conditions that can cause premature spoiling and adversely affect the quality, nature, and shelf life of the product. Even in the case of cold climate areas where the ambient temperatures are cool enough at certain times of the year to obviate the need for refrigerating the product, the product may need to be brought out of the ambient air temperature in order for the fumigant to be effective. Thus, in nearly every instance of ambient temperature fumigation, regardless of climate, the product will experience some type of uncontrolled temperature drop and/or spike during the fumigation process. As can be appreciated by those skilled in the art, exposure to swinging variations in temperature are detrimental to the quality of the product and, in some cases, will interrupt or upset the ripening stage of the product or cause the product to prematurely spoil.

In a further example, the harsh toxicity of the fumigants adversely affects the quality of the product and threatens the health and safety of the fumigators and the surrounding environment. Unfortunately, toxic concentrations of the fumigant settle on the treated product during fumigation and, during aeration of the fumigation enclosure, the residual fumigant gas is released into the open atmosphere where it settles on work surfaces and on the ground outside the fumigation site. Although fumigants are known to be highly toxic and exposure to certain fumigants is known to harm the shelf life of fresh fruits and vegetables, as well as the viability of dormant and actively growing plants and the germination of seeds, the USDA, in its Treatment Manual, states that the adverse affect "is a necessary risk in order to control pests." Therefore, the USDA, for example, requires that the fumigation site be located in an area that is isolated and can be secured to prohibit and/or restrict traffic and people from entering within a certain perimeter surrounding the site. Thus, while the USDA requires that there be a particular surrounding perimeter of, for example, 200 feet, in which access to the site is limited or forbidden (especially in areas downwind of the exhaust duct), there currently are no requirements that the fumigants be substantially filtered or removed from the exhaust air before it is expelled into the atmosphere. Therefore, given the choice, many fumigation operators do not take any steps to clean the exhaust air in order to forgo the additional high costs associated with the cleanup. To aerate the fumigation enclosure, operators simply remove the tarp, open the container or chamber doors, or force the exhaust through a duct and into the atmosphere by running their exhaust systems. Without taking any steps to actively remove the fumigant from the exhaust, the air circulation or exhaust system is relied upon to aerate the fumigation enclosure and bring the concentration of toxic gas inside the fumigation enclosure to within acceptable levels. Accordingly, this process takes a significant amount of time to complete (approximately 4 hours) and, to minimize the risk of harmful exposure to persons nearby the fumigation site, aeration must typically wait until activity around the fumigation site is at its least. As a result, the number of fumigation cycles that can be carried out during the course of a day is limited.

Accordingly, a need exists to overcome the problems discussed above.

SUMMARY OF THE INVENTION

As described above, it would be beneficial to incorporate a temperature control capability into a regulatory-compliant fumigation process to precisely and consistently control the temperature to which an agricultural product is exposed throughout the full fumigation cycle to preserve the product's quality, freshness, and shelf life.

In combination with the temperature control capability, it would be beneficial to incorporate a filtration capability into a regulatory-compliant fumigation process to filter the air of significant levels of the fumigant prior to the air being exhausted into the atmosphere at the conclusion of the fumigation cycle. Generally, the objective is to preserve the health of the environment and the safety of those around the fumigation site, as well as dramatically decrease the need for a restrictive perimeter around the fumigation site and the length of the aeration period.

In addition, it would be beneficial for the filtration capability to be a closed-loop system such that the air exchanges that must occur for the air to be filtered do not disrupt the temperature conditions that are being maintained inside the fumigation enclosure (as well as the ability to maintain a pressure inside the fumigation enclosure, when relevant). By using a closed-loop system, the temperature-controlled air can be quickly reintroduced back into the fumigation enclosure after having being filtered without any significant change to its temperature.

In addition, it would be beneficial to incorporate an exhaust capability into a regulatory-compliant fumigation process that not only exhausts the air out of the fumigation enclosure at the completion of a fumigation cycle but also, at the same time, "recaptures" ambient air, adjusts its temperature, and supplies this temperature-controlled air back into the fumigation enclosure. By not just replacing the exhausted air with air at ambient temperatures, the temperature-controlled conditions within the fumigation enclosure can be maintained all the way through to completion of the full fumigation cycle.

With the foregoing and other objects in view, there is provided, in accordance with the present invention, a fumigation system, comprising at least one fumigation enclosure comprising an interior space in which products are received and fumigated, a temperature control system associated with the at least one fumigation enclosure and operated to maintain the air temperature of the interior space at a specific pre-determined temperature to prevent exposure of the products enclosed therein to temperature variations during fumigation, a fumigant distribution system associated with the at least one fumigation enclosure and operated to supply a fumigant into the interior space to fumigate the products enclosed therein, and a filtration system associated with the at least one fumigation enclosure and operated to substantially filter the fumigant out from the air of the interior space upon completion of fumigation and reintroduce the filtered air back into the interior space.

In accordance with another mode of the invention, there is further provided an exhaust system associated with the at least one fumigation enclosure, the exhaust system having at least one supply duct operated to take in ambient air from outside of the fumigation enclosure, to control temperature of the ambient air taken from the outside, and then to supply the temperature-controlled air to the interior space and at least one return duct operated to draw air out of the interior space and to exhaust the air outside of the fumigation enclosure.

In accordance with a further mode of the invention, there is also provided a contained work space containing the at least one fumigation enclosure.

In accordance with an added mode of the invention, the at least one supply duct of the exhaust system takes in ambient air from outside the work space and the at least one return duct of the exhaust system draws air out of the interior space of the at least one fumigation enclosure and into the atmosphere outside of the work space.

In accordance with an additional mode of the invention, the at least one fumigation enclosure is stationary.

In accordance with yet another mode of the invention, the at least one fumigation enclosure is a normal atmospheric pressure (NAP) chamber.

In accordance with yet a further mode of the invention, the temperature control system comprises a condenser unit positioned outside the at least one fumigation enclosure, at least one cooling coil operatively connected to the condenser unit, at least one circulation fan positioned inside the interior space of the at least one fumigation enclosure and connected in line with the at least one cooling coil, and a feedback control system comprising at least one temperature sensor positioned inside the interior space, the temperature sensor operated to measure and transmit a temperature reading of the interior space used by the feedback control system to control operation of the temperature control system.

In accordance with another mode of the invention, the fumigant distribution system comprises one or more distribution nozzles inside the interior space of the at least one fumigation enclosure, at least one tank positioned outside the at least one fumigation enclosure and containing fumigant in the form of a compressed liquid, at least one volatilizer connected in line with the tank and operated to receive the liquid fumigant from the at least one tank and convert the liquid fumigant into its gaseous state, and at least one gas induction line having a proximal end in line with the volatilizer and a distal end inside the interior space of the at least one fumigation enclosure and connected to the one or more distribution nozzles such that, when the fumigant distribution system is operating, the gaseous fumigant flows from the at least one volatilizer through the at least one gas induction line and is released into the interior space through the one or more distribution nozzles.

In accordance with a further mode of the invention, the filtration system comprises at least one filtration tank having at least one carbon absorption element operated to remove the fumigant from air flowing therethrough, at least a first duct connected with the at least one filtration tank to supply fumigant-containing air from the interior space of the fumigation enclosure into the at least one filtration tank, at least a second duct connected with the at least one filtration tank to reintroduce back into the interior space the air that has filtered through the at least one carbon absorption element, and at least one fan positioned in line with the at least one filtration tank and operated to force the air from the interior space into the first duct, through the at least one filtration tank, and through the second duct.

In accordance with an added mode of the invention, the filtration system further comprises a feedback control system having at least one chemical sensor positioned inside the interior space of the at least one fumigation enclosure, the chemical sensor operated to measure and transmit a fumigant concentration reading of the air of the interior space used by the feedback control system to control the operation of the at least one fan.

In accordance with an additional mode of the invention, the filtration system comprises a first filtration tank and a second filtration tank interconnected by at least one interconnecting air duct, each of the first and second filtration tanks having at least one carbon absorption element operated to remove fumigant from air flowing therethrough, at least a first duct connected with the first filtration tank to supply fumigant-containing air from the interior space of the fumigation enclosure into the first filtration tank, at least a second duct connected with the second filtration tank to reintroduce back into the interior space the air that has filtered through the carbon absorption elements of the first and second filtration tanks, and at least one fan positioned in line with the first and second filtration tanks and operated to force the air from the interior space into the first duct, through the first filtration tank, through the interconnecting air duct, through the second filtration tank, and through the second duct.

In accordance with yet another mode of the invention, the filtration system is a closed-loop system such that the temperature of the air that is filtered and reintroduced back into the interior space of the fumigation enclosure remains substantially the same as the specific pre-determined temperature of the air inside the interior space.

In accordance with yet a further mode of the invention, the exhaust system further comprises a series of interconnected supply and exhaust circulation fans, outside-air and exhaust-air motorized dampers, one or more cooling coils, and one or more air filters.

In accordance with another mode of the invention, operation of the temperature control system, fumigant distribution system, filtration system, and exhaust system are controlled through pre-programmed, fully-automated controls.

With the objects of the invention in view, there is also provided a method of conducting a fumigation cycle, comprising providing at least one fumigation enclosure, the at least one fumigation enclosure having an interior space and, in association with the at least one fumigation enclosure, providing a temperature control system operated to substantially maintain the air temperature of the interior space at a specific pre-determined temperature, a fumigant distribution system, and a filtration system; using the temperature control system, bringing the air temperature of the interior space to the specific pre-determined temperature and substantially maintaining that temperature throughout the entire fumigation cycle; loading a product within the interior space of the fumigation enclosure; closing and sealing the fumigation enclosure such that it is airtight; using the fumigant distribution system, distributing fumigant within the interior space until concentration of the fumigant in the air of the interior space has reached a first pre-determined chemical concentration set point; and using the filtration system, substantially filtering the fumigant out from the air of the interior space and reintroducing the filtered air back into the interior space until concentration of the fumigant in the air of the interior space has reached a second pre-determined chemical concentration set point.

In accordance with another mode of the invention, there is also provided an exhaust system in association with the at least one fumigation enclosure, the exhaust system having at least one supply duct operated to supply air to the interior space and at least one return duct operated to draw air out of the interior space and to expel the air outside of the at least one fumigation enclosure. Using the exhaust system, exhaust air is drawn from inside the interior space to outside the at least one fumigation enclosure until concentration of the fumigant in the air of the interior space has reached a third pre-determined chemical concentration set point, and simultaneously with the exhaust, ambient air is supplied into the at least one fumigation enclosure wherein the exhaust system brings the ambient air to the specific pre-determined temperature before introducing it into the at least one fumigation enclosure.

Although the invention is illustrated and described herein as embodied in systems and processes for the fumigation of perishable agricultural products, whereby the fumigation is conducted under temperature-controlled conditions and incorporates air filtration, reintroduction, exhaust, and recapture capabilities, it is, nevertheless, not intended to be limited to the details shown because various modifications and structural changes may be made therein without departing from the spirit of the invention and within the scope and range of equivalents. Additionally, well-known elements of exemplary embodiments of the invention will not be described in detail or will be omitted to not obscure the relevant details of the invention.

Additional advantages and other features characteristic of the present invention will be set forth in the detailed description which follows and may be apparent from the detailed description or may be learned by practice of exemplary embodiments of the invention.

Other features that are considered as characteristic for the invention are set forth in the appended claims.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to further illustrate various embodiments and to explain various principles and advantages all in accordance with the present invention. Advantages of embodiments of the present invention will be apparent from the following detailed description of the exemplary embodiments thereof, which description should be considered in conjunction with the accompanying drawings in which:

FIG. 3B is a fragmentary, front elevational view of another exemplary embodiment of a filtration system of the fumigation system of FIG. 1;

FIG. 4 is a cross-sectional view of an exhaust section of an exhaust system of the fumigation system of FIG. 1;

DETAILED DESCRIPTION OF THE INVENTION

Figure 1:
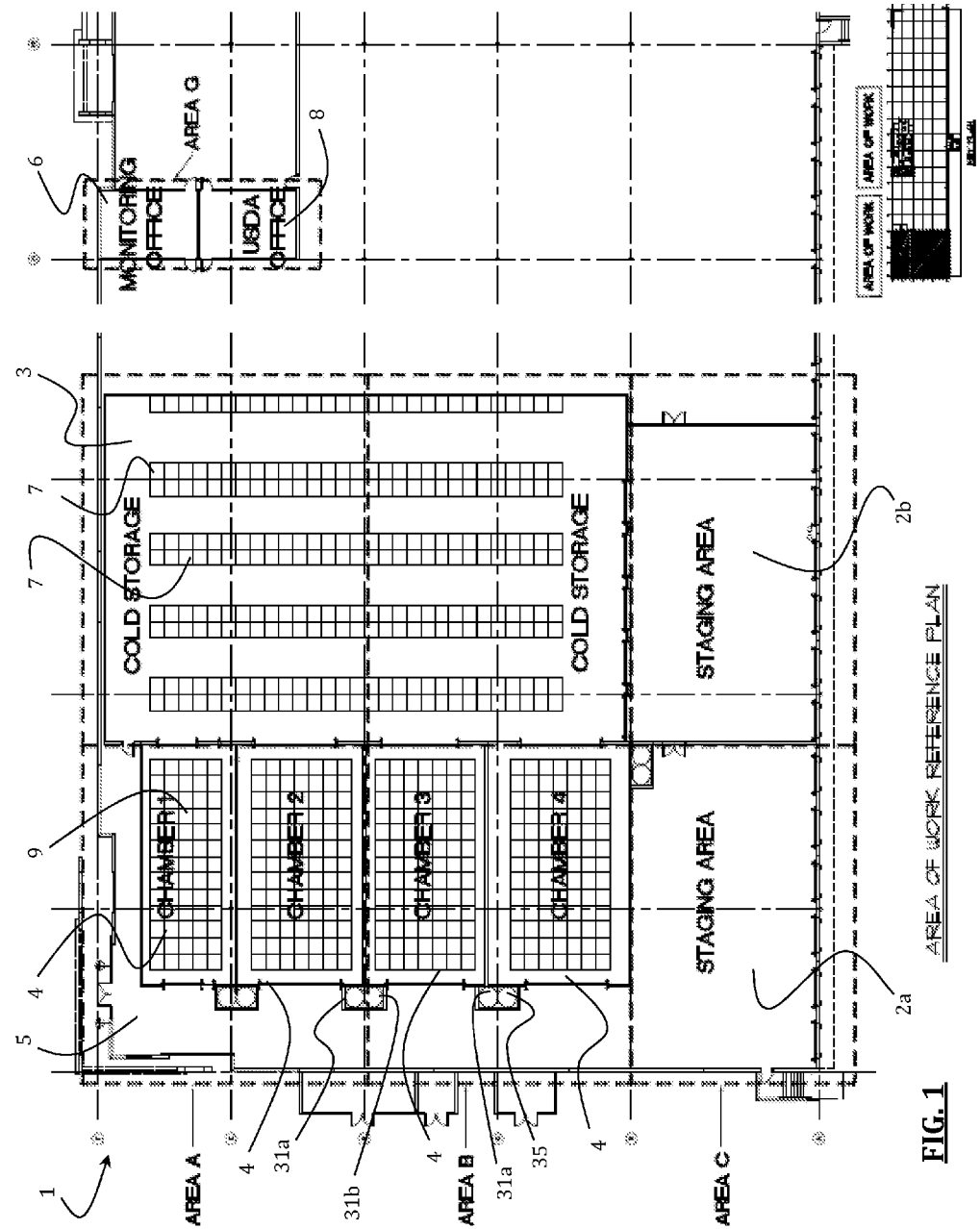
FIG. 1 is a partially hidden top plan view of a warehouse facility having a fumigation system, according to an exemplary embodiment of the present invention.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for any claims and as a representative basis for teaching one skilled in the art to variously employ the present invention in virtually any appropriately detailed structure. Further, the terms and phrases used herein are not intended to be limiting; but rather, to provide an understandable description of the invention. While the specification may conclude with claims defining the features of the invention that are regarded as novel, it is believed that the invention will be better understood from a consideration of the following description in conjunction with the drawing figures, in which like reference numerals are carried forward.

Before the present invention is disclosed and described, it is to be understood that the terminology used herein is for the purpose of describing particular embodiments only and is not intended to be limiting. The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled," as used herein, is defined as connected, although not necessarily directly, and not necessarily mechanically. Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

In the several exemplary embodiments described below, there are a number of references to the United States Department of Agriculture (USDA) where regulatory rules and operations are mentioned. These references to the USDA are only to illustrate just one example of a relevant regulatory agency. The present invention is in no way intended to be limited in its application to only the jurisdiction of the USDA.

Additionally, in the several exemplary embodiments described below, the present invention is used in conjunction with a normal atmospheric pressure (NAP) chamber (as defined and prescribed by the USDA). While the fumigation chamber process is generally regarded as the most effective treatment for penetrating densely packed or absorbent goods or when a relatively rapid turnover of the goods is required, the present invention is not limited to just use with a NAP chamber. To the contrary, the present invention is applicable to all types of regulatory-compliant fumigation enclosures, irrespective of whether they are specifically mentioned herein.

Described now is an exemplary embodiment of a fumigation system according to the present invention.

In FIG. 1, there is depicted an exemplary floor layout of a fumigation site 1 inside a warehouse facility. The warehouse facility may be located at any site where commodities, such as agricultural products, are imported and received and/or exported and transported out. These sites include, but are not limited to, any port of entry such as airports, land border checkpoints, railway depots, and air or sea shipping docks or ports. The fumigation site 1 is comprised of a number of areas that are insulated from one another by sealed doors and walls, or any other type of suitable barrier, such that each area can hold its own temperature and cross-contamination between the areas is prevented. These areas may include, but are not limited to, one or more temperature-controlled staging areas 2a, 2b, cold storage areas 3, and one or more fumigation chambers 4 within a designated work area 5. These various areas may be arranged in any manner suitable for the specific facility and their use.

Located in proximity to the fumigation site 1 is a monitoring location 6. The monitoring location 6 contains all of the equipment (e.g., boards, panels, displays, and controls) used by the operators to remotely monitor and operate the fumigation system. In this particular embodiment, the fumigation system is fully automated and programmed to implement all of the various stages of the fumigation procedure in accordance with agency regulations. Alternatively, the fumigation system may be operated using manual controls or a combination of both manual and automated controls. This monitoring location 6 may also include an office location 8 for the oversight regulatory agency (e.g., the USDA). This office location 8 is provided as a base for USDA inspection and monitoring officials to carry out their regulatory duties for the fumigation process.

Staging area 2a is for the quarantine of incoming cargo 9 before it is fumigated. Incoming cargo pallets, or entire shipping containers containing multiple cargo pallets, are unloaded into a temperature-controlled staging area 2a to await fumigation. Eventually, to undergo fumigation, the cargo 9 is moved out of staging area 2a and loaded into the one or more fumigation chambers 4 of work area 5 in accordance to specific regulatory protocols. As mentioned above, work area 5 could be temperature-controlled such that the open space surrounding the one or more fumigation chambers 4 may be temperature-controlled as well.

Figure 2:
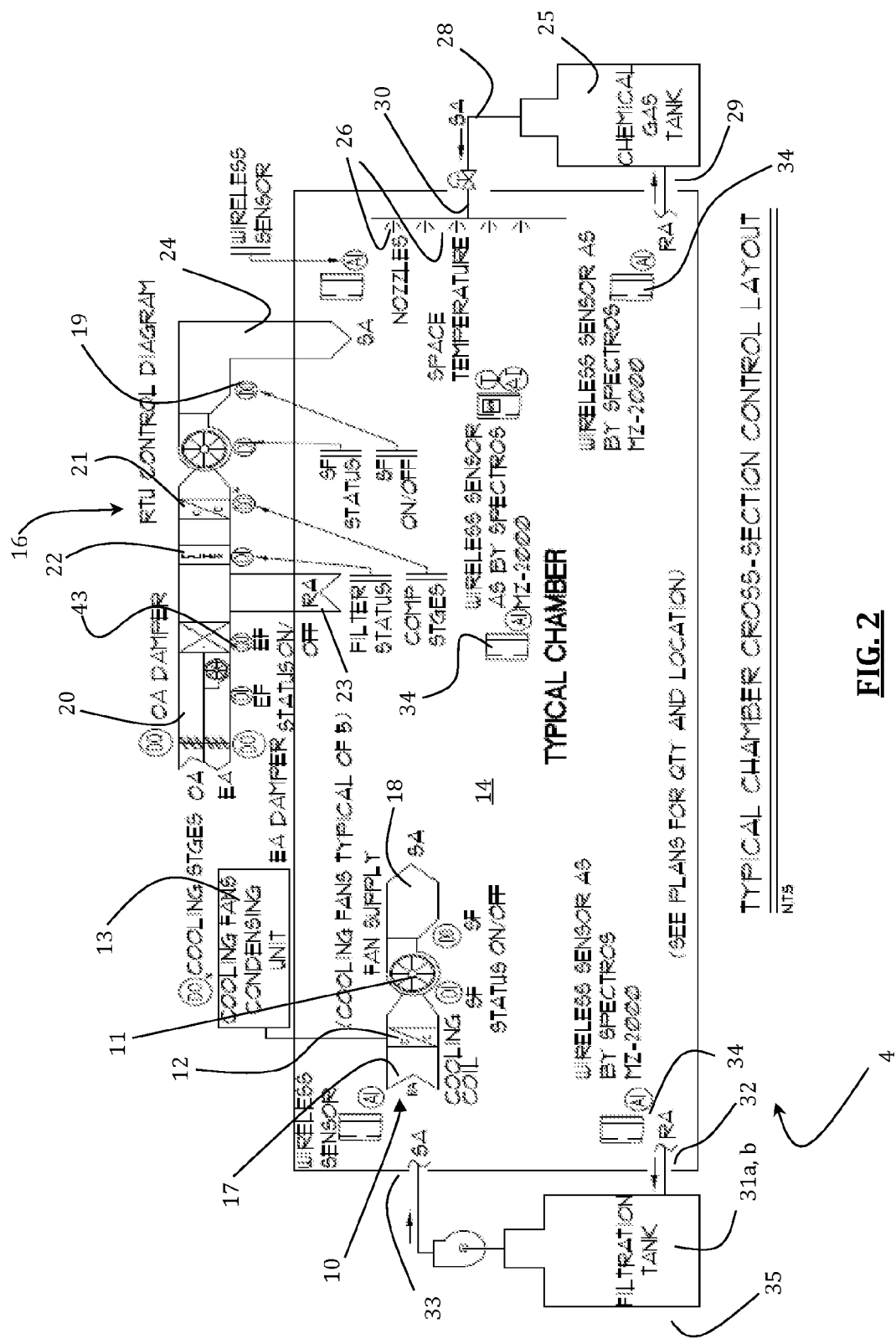
FIG. 2 is a cross-sectional view of a fumigation chamber of the fumigation system of FIG. 1.

In FIG. 2, there is shown a cross-sectional layout of an exemplary fumigation chamber 4 illustrating the several contemplated systems of the overall fumigation system, in accordance with an exemplary embodiment of the present invention. In this particular depiction, the chamber 4 is vacant and does not contain any cargo 9 to be treated. As mentioned above, in this particular embodiment, the fumigation system of the present invention is described in conjunction with a normal atmospheric pressure (NAP) chamber. However, the fumigation system of the present invention may be used in conjunction with any type of fumigation enclosure that is compliant with any necessary regulatory provision(s) and can be retrofitted to have all of the necessary components of the fumigation system of the present invention. Also, ideally, the fumigation enclosure (e.g., chamber 4) should not be specific to any one type or kind of commodity or agricultural product.

To control the temperature of the air inside the interior space 14 of the chamber 4, the fumigation system comprises a temperature control system 10. The temperature control system 10 sets the air temperature within the chamber at a specific temperature (or temperature range) that is best suited for the effectiveness of the fumigant and consistently maintains this temperature (or range) to prevent the agricultural product (or, generally, any other treated product) from being exposed to temperature variations during the fumigation process that will ultimately harm the quality and longevity of the product. For purposes of the exemplary embodiment shown in FIG. 2, the temperature control system 10 is, for example, a refrigeration (or cooling) unit that is comprised of one or more circulation "cooling" fans 11 that maintain a pre-determined temperature inside the chamber 4 by selectively cooling the air of the interior space 14 of the chamber 4 at various stages or throughout the entire fumigation process. However, the temperature control system 10 is not limited to being a refrigeration unit and may be configured to have a heating element or both cooling and heating elements for the selective heating and cooling of the interior space 14 as dictated by the surrounding climate of the fumigation site 1. As shown in detail in FIG. 2, the one or more circulation fans 11 are connected in line with at least one cooling coil 12. In turn, the cooling coil 12 is connected to a condenser unit 13 located outside of the chamber 4. When running, the circulation fans 11 circulate air throughout the chamber 4. If it is needed to cool the air circulating through the temperature control system 10, the at least one cooling coil 12 is activated. Likewise, in embodiments of the temperature control system 10 that incorporate a heating element, the heating element can be activated to heat the air circulating through the temperature control system 10 when needed. In other words, unless a cooling and/or heating element of the temperature control system 10 is activated, the fans 11 may be used to simply circulate the air within the interior space 14 of the chamber 4.

With respect to the fumigant, there exist a variety of fumigants. In the United States, only three types of fumigants are approved by the USDA—Methyl bromide (MB), Sulfuryl fluoride (SF), and Phosphine (PH). As is understood by those skilled in the art, the fumigant is typically stored as a compressed liquid inside a metal cylinder tank. Before introducing the fumigant into the fumigation enclosure at the appropriate stage of the fumigation cycle, the fumigant is typically heated using a volatilizer (or vaporizer) and converted into a gas. Once the fumigant is fully converted into its gaseous state, it is released and distributed within the fumigation enclosure. In the exemplary embodiment of FIG. 2, the liquid fumigant is stored inside tank 25 that is positioned proximal the chamber 4. The internal pressure of the tank 25 forces the fumigant through a volatilizer (not shown) and, ultimately, through an insulated copper pipe 28 (such that the fumigant remains in a gaseous state) and into at least one gas induction line 30 that enters the chamber 4. The gas induction line 30 is connected to a plurality of nozzles 26 that are positioned within the chamber 4 and, when opened, release the fumigant gas into the interior space 14. In this exemplary embodiment, the nozzles 26 are positioned on one side of the chamber 4. However, the nozzles 26 may be strategically positioned anywhere within the chamber 4. As is understood by persons of skill in the art, the weight of the fumigant gas is generally heavier than that of the air. As a result, the one or more circulation fans are used to circulate the air to ensure the upward movement and distribution of the fumigant gas as soon as it is expelled from the nozzles 26.

Figure 3A:
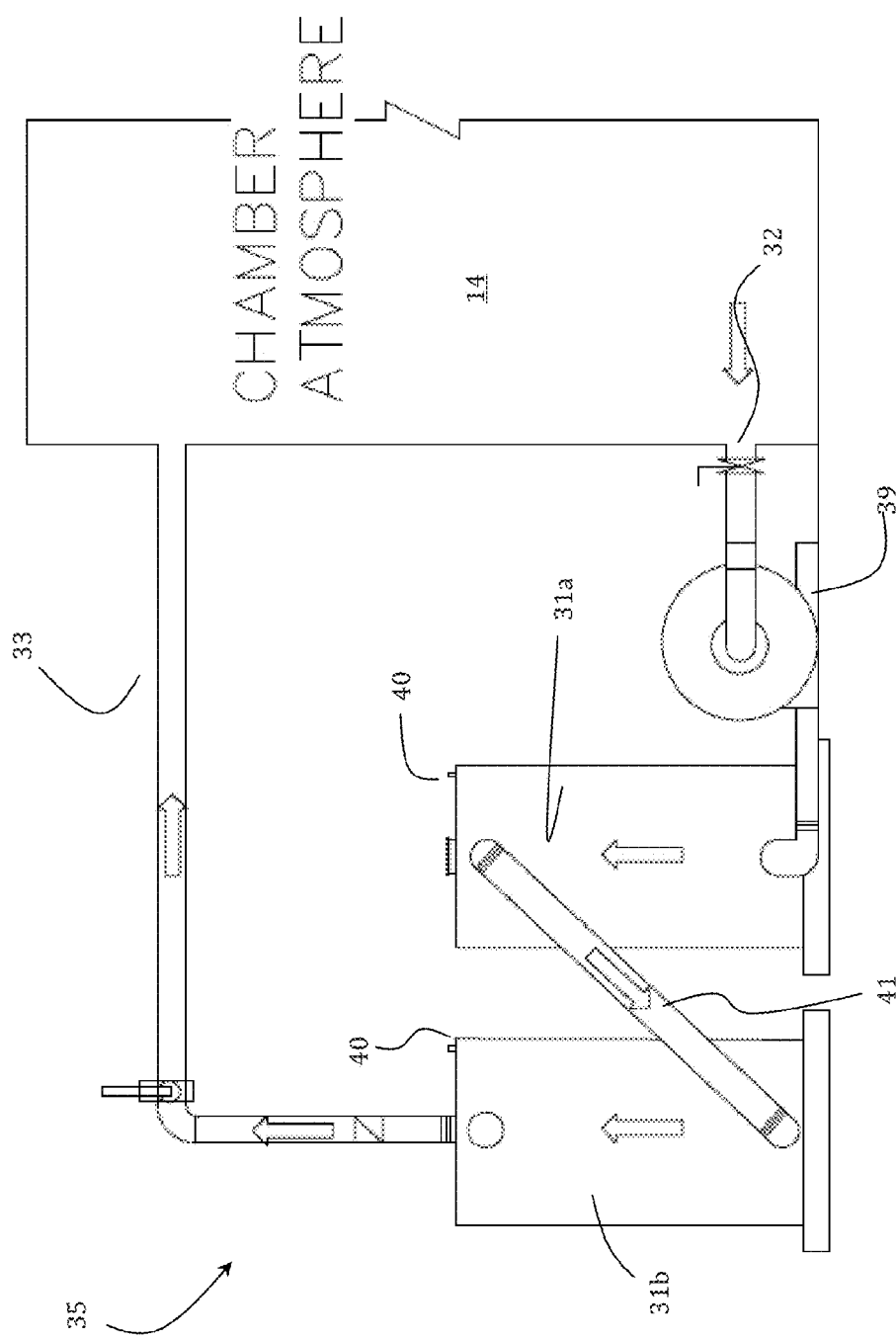
FIG. 3A is a fragmentary, front elevational view of an exemplary embodiment of a filtration system of the fumigation system of FIG. 1.

Subsequently thereafter, once the air of the interior space 14 of the chamber 4 has become saturated with the fumigant and the fumigant has taken its necessary effect, embodiments of the present invention provide a filtration system 35 that substantially removes the fumigant from the air before the air is exhausted out from the chamber 4 and into the open atmosphere. In FIGS. 3A and 3B, there is shown an exemplary embodiment of the filtration system 35. The filtration system is comprised of at least one filtration tank that is located, for example, just outside the chamber 4. In other embodiments, the at least one filtration tank may be located entirely within the chamber 4. In this particular configuration, the filtration system 35 is comprised of two separate tanks 31a, 31b that are positioned in line with one another and interconnected by an air duct 41, each tank performing the same function. In each tank 31a, 31b, there is at least one carbon filter (not shown). However, any type of filtration media that is absorptive and is capable of substantially removing the fumigant from air flowing through it may be used inside the one or more filtration tanks. Carbon filters that are suitable for use in the present invention are commercially available and can be found, for example, under the names TIGG™ and NORDIKO™. These carbon filters, when used according to certain specifications, have been shown to substantially remove or lessen the concentration of certain known fumigants from ambient air. Located adjacent to the tanks is a fan 39 that draws air out from chamber atmosphere and into the first filtration tank 31a through at least one RA duct (or plenum) 32. FIGS. 3A and 3B depict possible arrangements for the fan 39. The air is forced through the first filtration tank 31a and then, via the interconnecting air duct 41, is forced through the second filtration tank 31b, thereby filtering the air of the fumigant. At this point, the air, now having been filtered, is not released into the atmosphere. Rather, at least one SA duct (or plenum) 33 creates a closed-loop system that reintroduces the filtered air back into the chamber atmosphere. Thus, the filtration system 35 cleans the air and reintroduces the air back into the chamber without any significant change in the temperature of the circulated air. Accordingly, the temperature-controlled conditions within the chamber 4 are efficiently maintained despite the introduction of the filtration system 35. As described in detail below, the fan 39 continues to circulate the air through the filtration system 35 until the concentration of the fumigant in the air has dropped to a pre-determined level.

After a certain number of uses, the filtration media of the filtration system become saturated and, in the case of carbon filters, they must be removed and replaced with, for example, a new carbon filter or a used carbon filter that has been rehabilitated. In the exemplary embodiment of FIG. 3, there exist one or more monitoring ports 40 that are visible from the outside of each tank 31a, 31b to allow an operator to see the saturation of the filters and determine their effectiveness and need for replacement.

As described above, at the completion of a fumigation cycle, the fumigation enclosure is typically aerated into the open atmosphere before the product may be safely removed from the fumigation enclosure at the end of the process. This aeration step may be conducted passively by simply opening up the fumigation enclosure and allowing it to air out. Or, it may be conducted actively by using an exhaust system. In the present invention, the filtration system 35 may be run until there is a near-zero concentration of the fumigant remaining in the chamber interior and, therefore, drastically shorten or entirely eliminate the need to exhaust the air from the chamber interior. However, depending on the local regulations of where the fumigation site resides and the operational and engineering considerations that vary from site to site, it may be beneficial to still employ an exhaust system in conjunction with the filtration system 35 as a method of removing the fumigant from the chamber interior. Referring back to FIG. 2, there is shown an exemplary embodiment of an exhaust system 16 according to the present invention. In this particular configuration, portions of the exhaust system 16 are located on the outside and at the "roof top" of the chamber 4. The exhaust system 16 is comprised of a series of interconnected supply (SF) and exhaust (EF) circulation fans 19, 43, OA (outside-air) and EA (exhaust-air) motorized dampers 20, one or more cooling and/or heating coils 21, and air filters 22. In its "exhaust" capacity, the exhaust system 16 aerates (or purges) the interior space 14 of the chamber 4 into the open atmosphere. In FIG. 4, there is shown a cross-sectional view of the exhaust section of the exhaust system 16, according to an exemplary embodiment of the present invention. In this particular configuration, vents 55 connected to one or more RA (return-air) ducts (or plenums) 23 are positioned throughout the interior of the fumigation chamber 4. The one or more RA ducts (or plenums) 23 exit both the chamber (through ceiling 50) and the rooftop 60 of the fumigation site 1 itself. To aerate the chamber 4, air is drawn out from the interior of the chamber through the vents 55 and duct work 23 and, finally, out into the open atmosphere 70 through an exhaust stack 80.

Figure 5:
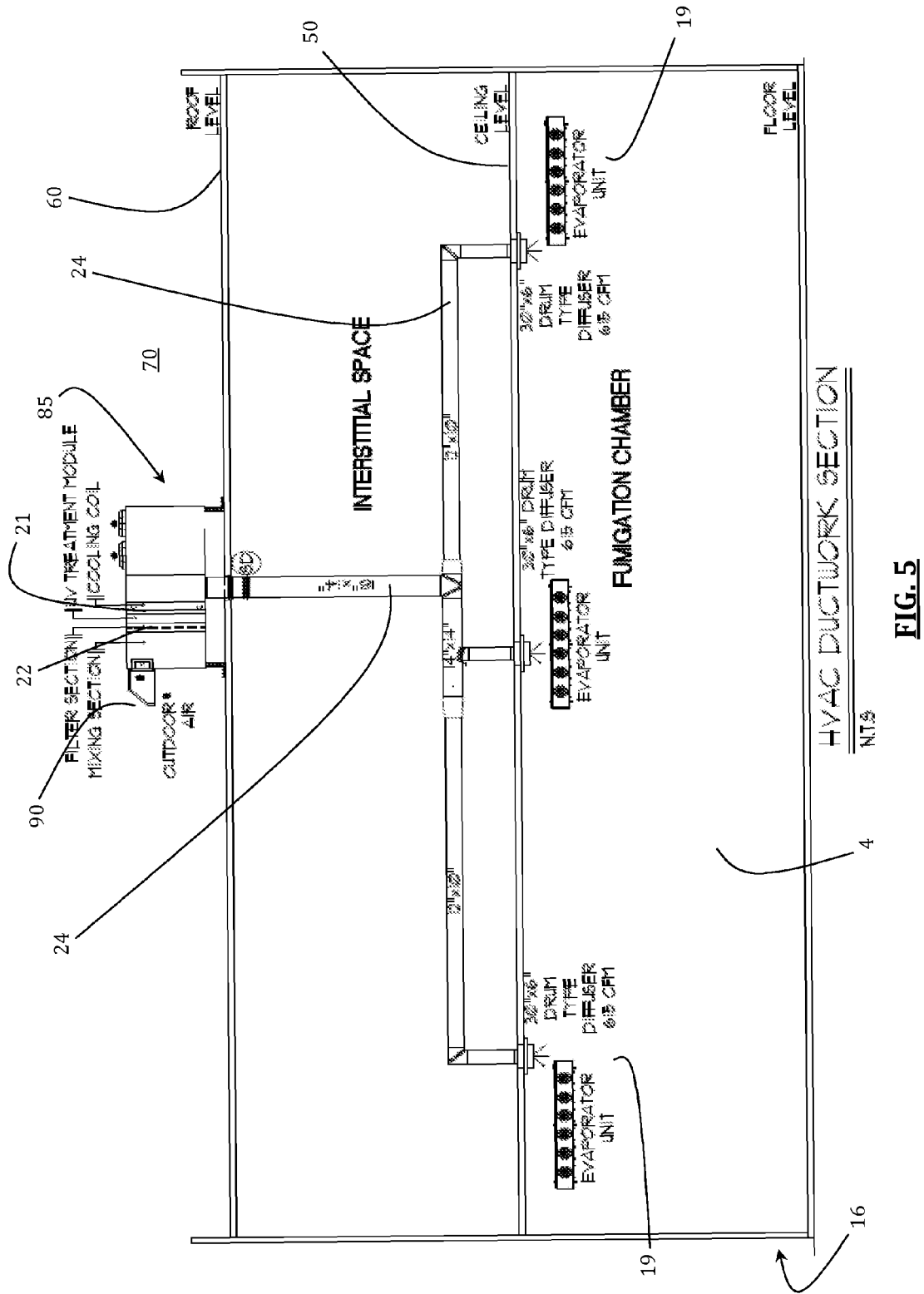
FIG. 5 is a cross-sectional view of an air supply section of an exhaust system of the fumigation system of FIG. 1.

In the reverse, in its "supply" capacity, the exhaust system 16 takes ambient air from the open atmosphere, adjusts its temperature, and supplies this air back into the chamber 4 to thereby, in essence, "recapture" or replace the temperature-controlled air lost during aeration of the chamber. This supplying of air back into the chamber occurs simultaneously while the chamber is being exhausted. In FIG. 5, there is shown a cross-sectional view of the supply section of the exhaust system 16, according to an exemplary embodiment of the present invention. In this particular configuration, one or more SA (supply-air) ducts (or plenums) 24 enter through the rooftop 60 of the fumigation site 1 and enter into the chamber 4 through its ceiling 50. The one or more SA ducts (or plenums) 24 are connected to a cooling and/or heating unit 85 located on the rooftop 60 of the fumigation site 1. The cooling and/or heating unit 85 is comprised of one or more cooling and/or heating coils 21. To supply air into the chamber 4, ambient air enters the cooling and/or heating unit 85 through an inlet 90 and is forced into the chamber 4 through the duct work 24 and is circulated by the circulation fans. When the one or more cooling and/or heating coils 21 are operating, the temperature of the ambient air being supplied into the chamber 4 by the exhaust system 16 can be controlled to be a specific temperature upon entering the chamber.

Accordingly, as shown in FIGS. 4 and 5, in this particular configuration, although the exhaust and the supply sections of the exhaust system 16 are separate and isolated from one another, they act simultaneously and in concert with each other to exchange the air inside the chamber 4 without compromising the temperature-controlled conditions within the chamber 4.

In the event of an emergency (e.g., a gas breach or leak), the exhaust system 16 may be configured to have an emergency exhaust capability. In addition, or alternatively, the filtration system 35 may be configured to include an exhaust port (not shown) that can be opened to the open atmosphere.

Each of the temperature control system 10, conversion, introduction, and dispersion of the fumigant, filtration system 35, and exhaust system 16 operate harmoniously and in conjunction with one another to complete the fumigation process. The entire process is intended to be performed through pre-programmed, fully-automated controls. However, alternatively, the process may be partially or fully manually operated using controls that are located at the equipment or at a location remote from the chamber 4 (such as the monitoring location 6). Important to the automation of the process, a plurality of gas and temperature sensors 34 are strategically positioned in the chamber 4 (including amongst the various systems such as at various locations within the filtration system) for providing various gas or chemical concentration measurements and temperature readings at determinative steps before, during, and after the fumigation process as a form of feedback control of the various systems of the fumigation system. These sensors 34 may be equipped with wireless capabilities that allow the sensors to wirelessly transmit and receive control signals and data to and from a remote location outside of the chamber.

Following the fumigation process and the successful aeration of the chamber 4 (described in detail below), the fumigated product 9 is unloaded from the chamber and immediately placed into refrigeration by moving it directly into the pest-free cold storage areas 3 (shown in FIG. 1) where it will await further transportation. In the event that the fumigated product must be dispatched immediately, the fumigated product may alternatively be placed into the pest-free temperature-controlled staging area 2b.

Figure 6:
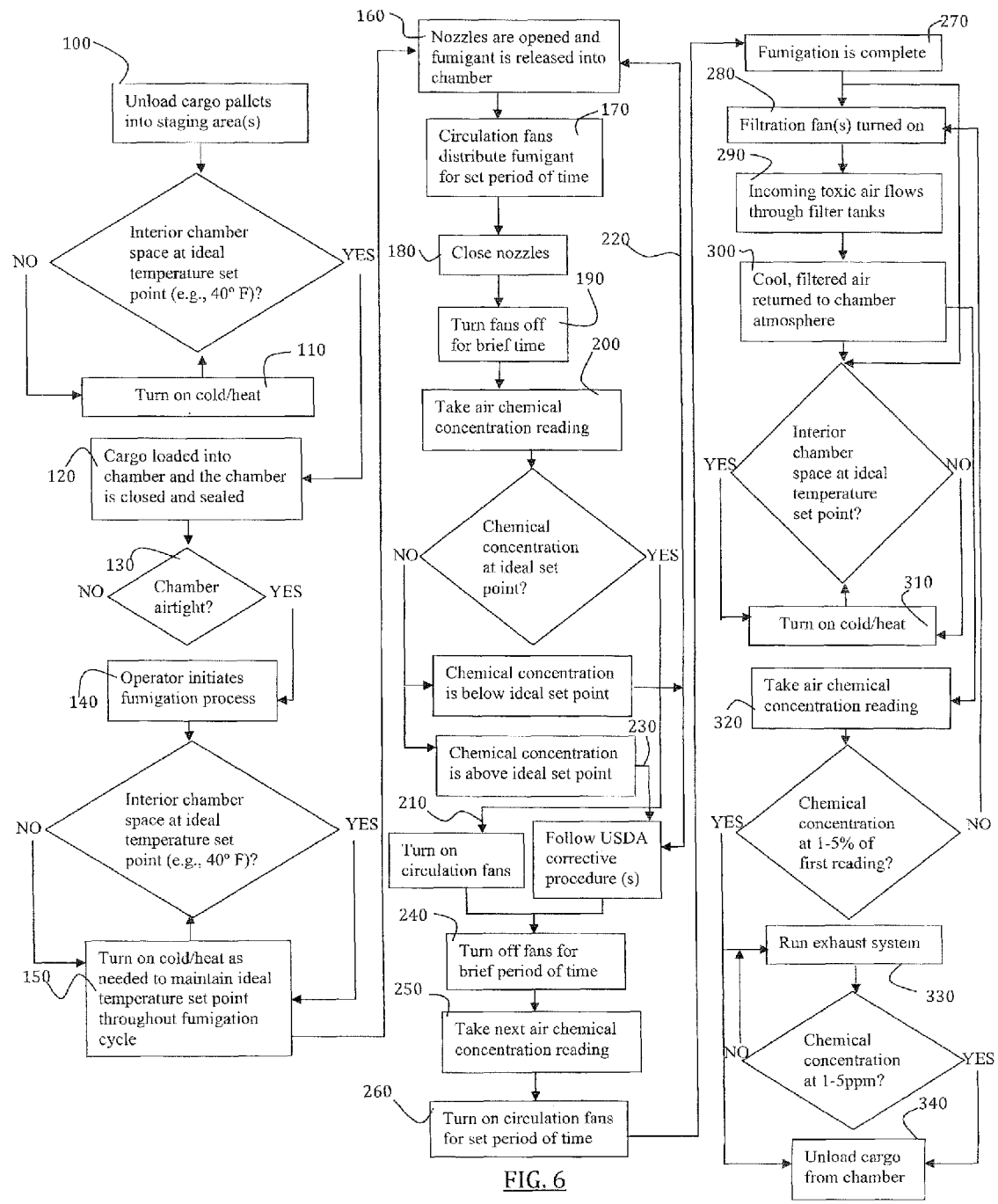
FIG. 6 is a flow diagram illustrating one complete fumigation cycle, according to an exemplary embodiment of the present invention.

In the form of a flow diagram, FIG. 6 illustrates, generally, the basic steps of an exemplary embodiment of an entire fumigation cycle that may be carried out with the systems of the present invention. Initially, at step 100, cargo of, for example, a perishable agricultural product is received and unloaded into a quarantined staging area 2a of the fumigation site 1. In this particular embodiment, the staging area(s) is/are consistently kept at a specific refrigeration temperature. For example, this temperature may be approximately 40° F. Concurrently therewith, the temperature within the interior space 14 of each fumigation chamber 4 is being consistently maintained at a specific temperature set point or range that is the minimum temperature (e.g., 40° F. to 50° F.) at which the fumigant is sufficiently effective (see steps 110 and 150) according to the USDA treatment schedule specific to the product being handled. Conversely, if the ambient air temperature is cooler than the specific temperature set point, the air must be heated. Prior to use of the chamber 4, the chamber 4 is inspected to ensure that it is airtight.

To fumigate the cargo, the cargo is loaded into the empty chamber at step 120. Once the cargo is satisfactorily loaded into the chamber 4 and the chamber is closed, the chamber is then sealed and a repeated inspection may be made to ensure that it is truly airtight (at step 130) whereby no gas leaks are present. Each chamber 4 is a sealed enclosure that is constructed of wall panels that are well insulated. If the chamber is not airtight or otherwise properly sealed, corrective action is required before proceeding with the fumigation process. At step 140, once the chamber 4 is adequately secured and airtight, an operator initiates the fumigation process, either by actuating one or more controls at the chamber 4 or from a remote location (e.g., the monitoring location 6).

As described above, during the entire fumigation cycle, the temperature of the interior of the chamber is being consistently maintained at a specific temperature set point or range using the temperature control system 10. To regulate the temperature within the chamber 4, the temperature control system 10 is feedback-controlled using the readings of the one or more temperature sensors 34 distributed throughout the chamber. The chamber is kept at this specific temperature set point or range in order to alleviate and/or prevent the product from being exposed to harmful temperature spikes or drops while, at the same time, still ensuring that the fumigant is released into the temperature conditions that are suitable for it to be effective. In some embodiments of the present invention, this specific temperature set point may be maintained within the chamber for a certain period of time (e.g., 30 minutes) before beginning fumigation.

To begin fumigation, the one or more nozzles 26 positioned inside the chamber 4 are opened and the fumigant is introduced into the chamber 4 (at step 160) in its gaseous form (after being converted) at a pre-determined rate (e.g., at 4 pounds (lbs) per 1,000 cubic feet). To effectively distribute the fumigant within the chamber 4, the circulation fans draw the fumigant upwards into the air and distribute the fumigant within the chamber for a pre-determined period of time (see step 170). After a specific period of distribution time has passed, the nozzles 26 are closed and all fans are turned off (at steps 180, 190) to begin the exposure period. After a brief period of time has passed, a first air chemical concentration reading of the chamber interior is taken (at step 200) using the sensor(s) 34.

If the sensor(s) 34 indicate that the air chemical concentration is within a desired, pre-determined specific concentration set point or range, the circulation fans 11 are turned back on (at step 210) in order to allow the temperature control system 10 to continue to actively control the temperature conditions within the chamber. If the concentration reading is below the desired set point or range, the nozzles 26 are again opened to allow more fumigant to be released into the chamber (at step 220), according to, for example, the corrective procedure(s) set forth in the USDA Treatment Manual. If the concentration reading is above the desired set point or range, there may be a corrective procedure in place as well, such as shortening the fumigation cycle (at step 230) (see, e.g., Table 2-4-6 of the USDA Treatment Manual). In simple terms, the concentration readings are conducted to ensure that the correct concentration of fumigant is maintained within the sealed chamber. On occasion that the reading is above the desired range, the fumigation period is shortened, or, on occasion that the reading is below the desired range, more fumigant is added and the fumigation cycle is extended according to USDA Treatment Manual protocols.

Once the pre-determined chemical concentration set point is reached, the circulation fans 11 re-circulate the air inside the chamber and the temperature control system 10 are active to substantially maintain the specific temperature set point or range for a pre-determined period of time until the next scheduled air chemical concentration reading occurs. For a brief time just prior to the next scheduled reading (and also according to USDA protocols), all fans 11 are turned off to settle the air to allow for an accurate second reading of the air chemical concentration within the chamber 4 (at steps 240, 250). If this second reading is the final reading (as it is according to USDA protocols), the circulation fans 11 are turned back on for a period of time to allow the temperature control system 10 to again actively control the temperature conditions within the chamber (at step 260) before the fumigation is considered complete (at step 270).

Although the exposure period of the fumigation is now complete, the air inside the chamber 4 is still saturated with the toxic fumigant. Accordingly, the filtration system 35 is actuated. At step 280, the fan 39 of the filtration system 35 is enabled (i.e., turned on) such that it draws the toxic air from inside the chamber out through the at least one RA duct (or plenum) 32 and through the serially-arranged filtration tanks 31a, b (see step 290). After the toxic air has flowed through both filtration tanks, the filtered air is reintroduced back into the chamber 4 through the at least one SA duct (or plenum) 33 (at step 300). And, as described in detail above, because the filtration system 35 is a closed-loop system that is sealed from the surrounding atmosphere, the filtered air that flows back into the chamber is still substantially at the temperature that is at or near the specific temperature set point or range being maintained inside the chamber itself. Meanwhile, although the temperature control system 10 is still controlling the temperature within the chamber (at step 310), it is being greatly aided by the reintroduction of the temperature-controlled air from the filtration system 35.

Continuing forward, the filtration system 35 and the temperature control system 10 continue to operate to filter, circulate and maintain the desired temperature of the air inside the chamber 4, until the sensors 34 indicate, at step 320, that the air chemical concentration reading of the fumigant level within the chamber atmosphere has fallen to within a range of 1% to 5% of the original chemical concentration reading taken at step 200. For example, based upon the specific configuration of the exemplary embodiment presently shown and described, this 1% to 5% value will be approximately between 150 and 750 ppm (parts-per-million). This particular concentration range may be based upon a number of factors. For example, this concentration level may be calculated based upon the local regulations specific to where the fumigation site is located. In another example, this concentration level may be determined by the point at which the amount of toxins remaining in the air of the chamber is at such a low level that the filters start to become less efficient in their ability to absorb any further toxins. In yet another example, this concentration level may be the concentration level at which, when the chamber is aerated into the open atmosphere outside of the fumigation site 1 by the exhaust system 16 (as described below) at a certain height and speed, the fumigant that does remain in the air is dissipated into the open atmosphere so quickly that it does not settle on the ground outside of the fumigation site. Accordingly, by use of the filtration system 35 according to the present invention and described herein, the need for a large restrictive perimeter surrounding the fumigation site and a lengthy aeration period is eliminated.

Lastly, to complete the fumigation cycle, the exhaust system 16 aerates the chamber space into the open atmosphere outside of the fumigation site 1 (at step 330). Specifically, the OA and EA motorized dampers 20 are opened and the one or more exhaust fans 43 are turned on in their "exhaust capacity" and allowed to run until the sensors 34 inside the chamber 4 indicate that the air chemical concentration reading of the fumigant within the chamber atmosphere has dropped even further to a regulatory agency stipulated specific non-toxic set point (e.g., between 1 and 5 ppm) and has been maintained for a specific period of time (e.g., 5 minutes). Concurrently, in their "supply capacity," the one or more supply fans 19 of the exhaust system 16 are turned on to supply temperature-controlled air from the ambient atmosphere back into the chamber 4 to replace the air being exhausted from the chamber. Accordingly, in conjunction with the temperature control system 10, the temperature-controlled conditions within the chamber 4 are efficiently maintained even during the aeration stage of the fumigation process. Once the final chemical concentration point has been reached, the chamber 4 may be unsealed and the fumigated cargo may be removed (at step 340) and placed into cold storage 3 or in staging area 2b.

As a result, the product has been fumigated, according to regulation, using systems and processes that maintain the product in a consistent cold (or otherwise temperature-controlled) chain throughout the fumigation cycle and substantially eliminate the toxicity typically associated with the existing methods of chemical fumigation.

Figure 7:
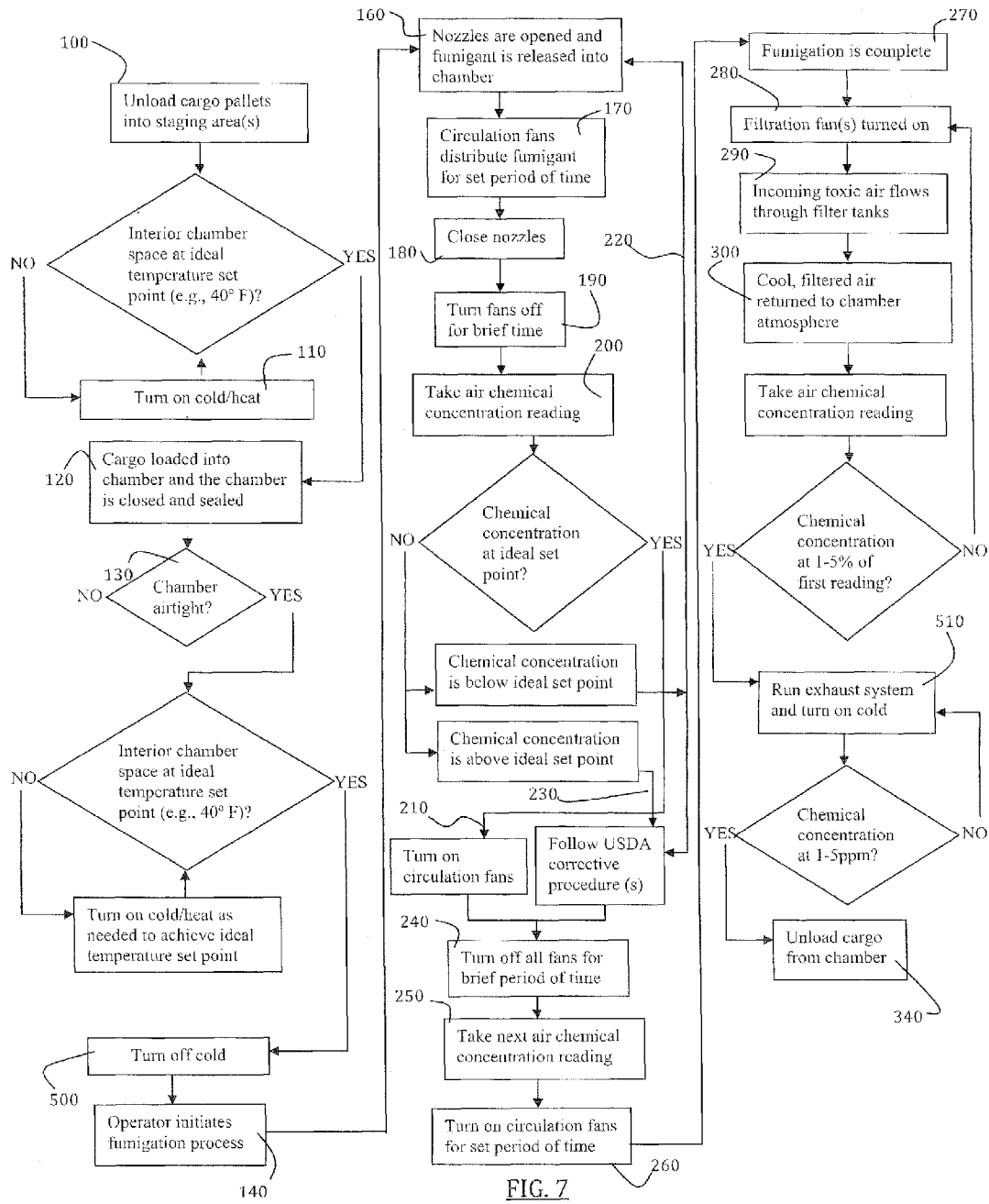
FIG. 7 is a flow diagram illustrating one complete fumigation cycle, according to another operation of the exemplary embodiment of FIG. 6.

In the flow diagram of FIG. 7, there is shown a slightly different operation of the fumigation system just described above. Similar to the operation shown in FIG. 6, the temperature of the air inside the chamber 4 is brought to a specific temperature set point or range prior to distributing the fumigant within the chamber 4 and is substantially maintained throughout the fumigation cycle. To accomplish this specific temperature set point (or range), it may be necessary in some instances for the actual cooling coils 12 of the temperature control system 10 to be set to a temperature that is several degrees cooler than the specific temperature set point (or range) of the chamber air itself. As a result, while the fumigant gas is present in the chamber 4, the lower temperature of the cooling coils 12 may cause the fumigant to condense or liquefy. Therefore, to prevent this unwanted circumstance, it may be beneficial that the actual cooling coils 12 of the temperature control system 10 remain off (at step 500) while the fumigant is present in the chamber air. Once the concluding aeration stage of the fumigation cycle begins, the cooling coils 12 may operate again (at step 510). However, the circulation fans 11 of the temperature control system 10 may, themselves, remain on throughout the appropriate stages of the fumigation cycle to act solely as a means of circulating the air within the chamber 4 (e.g., the circulation fans 11 are still used during the fumigant distribution period at step 170 and the circulation period at step 260). Despite the suspension of the cooling capability of the temperature control system 10, the interior space 14 of the chamber substantially maintains the set temperature point or range throughout the administration of the fumigant due to the chamber structure itself, which is well-insulated, sealed, and airtight. To further prevent fluctuations in the air temperature of the chamber, the surrounding work area 5 around the chamber 4 is kept at a temperature that is within a suitable range of the specific temperature set point or range of the interior of the chamber 4.

The foregoing description and accompanying drawing illustrate the principles, preferred embodiments and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention.

What is claimed is:

1. A fumigation system, comprising:
   at least one fumigation enclosure comprising an interior space in which products are received and fumigated;
   a temperature control system associated with the at least one fumigation enclosure and operated to maintain the air temperature of the interior space at a specific predetermined temperature to prevent exposure of the products enclosed therein to temperature variations during fumigation;
   a fumigant distribution system associated with the at least one fumigation enclosure and operated to supply a fumigant into the interior space to fumigate the products enclosed therein;
   a filtration system associated with the at least one fumigation enclosure and operated to:
      substantially filter the fumigant out from the air of the interior space upon completion of fumigation; and
      reintroduce the filtered air back into the interior space; and
   an exhaust system associated with the at least one fumigation enclosure, the exhaust system having:
      at least one supply duct operated to take in ambient air from outside of the fumigation enclosure, to control temperature of the ambient air taken from the outside, and then to supply the temperature-controlled air to the interior space; and
      at least one return duct operated to draw air out of the interior space and to exhaust the air outside of the fumigation enclosure.

2. The fumigation system according to claim 1, wherein operation of the temperature control system, fumigant distribution system, filtration system, and exhaust system are controlled through pre-programmed, fully or partially-automated controls.

3. A fumigation system, comprising:
   at least one stationary fumigation enclosure comprising an interior space in which products are received and fumigated;
   a temperature control system associated with the at least one fumigation enclosure and operated to maintain the air temperature of the interior space at a specific predetermined temperature to prevent exposure of the products enclosed therein to temperature variations during fumigation;
   a fumigant distribution system associated with the at least one fumigation enclosure and operated to supply a fumigant into the interior space to fumigate the products enclosed therein;
   a filtration system associated with the at least one fumigation enclosure and operated to:
      substantially filter the fumigant out from the air of the interior space upon completion of fumigation; and
      reintroduce the filtered air back into the interior space; and
   an exhaust system associated with the at least one fumigation enclosure, the exhaust system having:
      at least one supply duct operated to take in ambient air from outside of the fumigation enclosure, to control temperature of the ambient air taken from the outside, and then to supply the temperature-controlled air to the interior space; and
      at least one return duct operated to draw air out of the interior space and to exhaust the air outside of the fumigation enclosure.

4. The fumigation system according to claim 3, further comprising a contained work space containing the at least one fumigation enclosure.

5. The fumigation system according to claim 4, wherein:
the at least one supply duct of the exhaust system takes in ambient air from outside the work space; and
the at least one return duct of the exhaust system draws air out of the interior space of the at least one fumigation enclosure and into the atmosphere outside of the work space.

6. The fumigation system according to claim 3, wherein the at least one fumigation enclosure is a normal atmospheric pressure (NAP) chamber.

7. The fumigation system according to claim 3, wherein the temperature control system comprises:
a condenser unit positioned outside the at least one fumigation enclosure;
at least one cooling coil operatively connected to the condenser unit;
at least one circulation fan positioned inside the interior space of the at least one fumigation enclosure and connected in line with the at least one cooling coil; and
a feedback control system comprising at least one temperature sensor positioned inside the interior space, the temperature sensor operated to measure and transmit a temperature reading of the interior space used by the feedback control system to control operation of the temperature control system.

8. The fumigation system according to claim 3, wherein the fumigant distribution system comprises:
one or more distribution nozzles inside the interior space of the at least one fumigation enclosure;
at least one tank positioned outside the at least one fumigation enclosure and containing fumigant in the form of a compressed liquid;
at least one volatilizer connected in line with the tank and operated to receive the liquid fumigant from the at least one tank and convert the liquid fumigant into its gaseous state; and
at least one gas induction line having:
a proximal end in line with the volatilizer; and
a distal end inside the interior space of the at least one fumigation enclosure and connected to the one or more distribution nozzles such that, when the fumigant distribution system is operating, the gaseous fumigant flows from the at least one volatilizer through the at least one gas induction line and is released into the interior space through the one or more distribution nozzles.

9. The fumigation system according to claim 3, wherein the filtration system comprises:
at least one filtration tank having at least one carbon absorption element operated to remove the fumigant from air flowing therethrough;
at least a first duct connected with the at least one filtration tank to supply fumigant-containing air from the interior space of the fumigation enclosure into the at least one filtration tank;
at least a second duct connected with the at least one filtration tank to reintroduce back into the interior space the air that has filtered through the at least one carbon absorption element; and
at least one fan positioned in line with the at least one filtration tank and operated to force the air from the interior space into the first duct, through the at least one filtration tank, and through the second duct.

10. The fumigation system according to claim 9, wherein the filtration system further comprises a feedback control system positioned inside the interior space of the at least one fumigation enclosure, the feedback control system operated to measure a fumigant concentration of the air of the interior space and, based upon the measure fumigant concentration, control the operation of the at least one fan.

11. The fumigation system according to claim 3, wherein the filtration system comprises:
a first filtration tank and a second filtration tank interconnected by at least one interconnecting air duct, each of the first and second filtration tanks having at least one carbon absorption element operated to remove fumigant from air flowing therethrough;
at least a first duct connected with the first filtration tank to supply fumigant-containing air from the interior space of the fumigation enclosure into the first filtration tank;
at least a second duct connected with the second filtration tank to reintroduce back into the interior space the air that has filtered through the carbon absorption elements of the first and second filtration tanks; and
at least one fan positioned in line with the first and second filtration tanks and operated to force the air from the interior space into the first duct, through the first filtration tank, through the interconnecting air duct, through the second filtration tank, and through the second duct.

12. The fumigation system according to claim 11, wherein the filtration system further comprises a feedback control system having at least one chemical sensor positioned inside the interior space of the at least one fumigation enclosure, the chemical sensor operated to measure and transmit a fumigant concentration reading of the air of the interior space used by the feedback control system to control the operation of the at least one fan.

13. The fumigation system according to claim 3, wherein the filtration system is a closed-loop system such that the temperature of the air that is filtered and reintroduced back into the interior space of the fumigation enclosure remains substantially the same as the specific pre-determined temperature of the air inside the interior space.

14. The fumigation system according to claim 3, wherein the exhaust system further comprises:
a series of interconnected supply and exhaust circulation fans;
outside-air and exhaust-air motorized dampers;
one or more cooling coils; and
one or more air filters.

15. A method of conducting a fumigation cycle, comprising:
providing at least one fumigation enclosure, the at least one fumigation enclosure having an interior space and, in association with the at least one fumigation enclosure, providing:
a temperature control system operated to substantially maintain the air temperature of the interior space at a specific pre-determined temperature;
a fumigant distribution system;
a filtration system; and
an exhaust system;
using the temperature control system, bringing the air temperature of the interior space to the specific pre-determined temperature and substantially maintaining that temperature throughout the entire fumigation cycle;
loading a product within the interior space of the fumigation enclosure;
closing and sealing the fumigation enclosure such that it is airtight;

using the fumigant distribution system, distributing fumigant within the interior space until concentration of the fumigant in the air of the interior space has reached a first pre-determined chemical concentration set point;

using the filtration system, substantially filtering the fumigant out from the air of the interior space and reintroducing the filtered air back into the interior space until concentration of the fumigant in the air of the interior space has reached a second pre-determined chemical concentration set point; and using the exhaust system:

drawing exhaust air from inside the interior space to outside the fumigation enclosure until concentration of the fumigant in the air of the interior space has reached a third pre-determined chemical concentration set point; and simultaneously with the exhaust, supplying ambient air from outside of the fumigation enclosure into the interior space wherein the exhaust system controls the temperature of the ambient air before introducing it into the interior space.

16. The method according to claim 15, wherein the exhaust system comprises:

at least one supply duct operated to supply the temperature-controlled ambient air to the interior space; and at least one return duct operated to draw air out of the interior space and to expel the air outside of the at least one fumigation enclosure.

17. The method according to claim 15, wherein the filtration system is a closed-loop system such that the temperature of the air that is filtered and reintroduced back into the interior space of the fumigation enclosure remains substantially the same as the specific pre-determined temperature of the air inside the interior space.

18. The method according to claim 15, wherein the at least one fumigation enclosure is stationary.

* * * * *